(12) United States Patent
Brehm (10) Patent No.: US 9,005,302 B2
(45) Date of Patent: Apr. 14, 2015

(54) MODULAR HIP IMPLANT

(75) Inventor: Peter Brehm, Weisendorf (DE)

(73) Assignee: Peter Brehm GmbH, Weisendorf (DE)

( * ) Notice: Subject to any disclaimer, the term of this patent is extended or adjusted under 35 U.S.C. 154(b) by 345 days.

(21) Appl. No.: 12/297,348

(22) PCT Filed: Apr. 18, 2007

(86) PCT No.: PCT/EP2007/003408
§ 371 (c)(1),
(2), (4) Date: Oct. 16, 2008

(87) PCT Pub. No.: WO2007/118708
PCT Pub. Date: Oct. 25, 2007

(65) Prior Publication Data
US 2009/0088865 A1    Apr. 2, 2009

(30) Foreign Application Priority Data

Apr. 19, 2006 (DE) .......................... 20 2006 006 349

(51) Int. Cl.
*A61F 2/34* (2006.01)
*A61F 2/30* (2006.01)
(Continued)

(52) U.S. Cl.
CPC ............ *A61F 2/30744* (2013.01); *A61B 17/86* (2013.01); *A61F 2/34* (2013.01); *A61F 2/4637* (2013.01);
(Continued)

(58) Field of Classification Search
CPC ...................................... A61F 2/34; A61F 2/32
USPC ................................ 623/22.42, 22.11–22.39
See application file for complete search history.

(56) References Cited

U.S. PATENT DOCUMENTS 5,108,445 A    4/1992  Ashby
5,108,448 A    4/1992  Gautier
(Continued)

FOREIGN PATENT DOCUMENTS

CN    1 533 262 A     9/2004
DE    41 02 510 A1    7/1992
(Continued)

OTHER PUBLICATIONS

Ottersbach, A. et al., Optimization of Cup Positioning in THA-Comparison between Conventional Mechanical Instrumentation and Computer-Assisted Implanted Cups by using the Orthopilot Navigation System; Z. Orthop. Ihre Grenzgeb. 2005; 143: 611-615; Abstract.

(Continued)

*Primary Examiner* — Thomas J Sweet
*Assistant Examiner* — Christopher D Prone
(74) *Attorney, Agent, or Firm* — Parsons Summa (57) ABSTRACT

A modular hip implant is disclosed that includes a base member that is to be attached to a pelvic bone, and a cup for accommodating a hip joint prosthesis. The base member is provided with fasteners for mounting the base member on the pelvic bone as well as a concave accommodation portion for the cup. The cup has a convex outer shape which is complementary to the accommodation portion such that the radii of curvature determining the concave accommodation portion and the convex outer form essentially correspond to each other and the cup can be attached within the base member. The base member and/or the cup include adjustment means for adjusting the position of the cup relative to the base member. The invention allows the inclination and anteversion to be adjusted by arranging the cup in the base.

8 Claims, 10 Drawing Sheets

(51) Int. Cl.
*A61F 2/46* (2006.01)
*A61B 17/86* (2006.01)

(52) U.S. Cl.
CPC .......... *A61F 2002/30143* (2013.01); *A61F 2002/30327* (2013.01); *A61F 2002/30403* (2013.01); *A61F 2002/30405* (2013.01); *A61F 2002/30416* (2013.01); *A61F 2002/30426* (2013.01); *A61F 2002/30433* (2013.01); *A61F 2002/30449* (2013.01); *A61F 2002/30489* (2013.01); *A61F 2002/30538* (2013.01); *A61F 2002/30542* (2013.01); *A61F 2002/30576* (2013.01); *A61F 2002/30578* (2013.01); *A61F 2002/30604* (2013.01); *A61F 2002/30616* (2013.01); *A61F 2002/30774* (2013.01); *A61F 2002/30787* (2013.01); *A61F 2002/3401* (2013.01); *A61F 2002/3403* (2013.01); *A61F 2002/3404* (2013.01); *A61F 2002/3411* (2013.01); *A61F 2002/343* (2013.01); *A61F 2002/3432* (2013.01); *A61F 2002/3441* (2013.01); *A61F 2002/3443* (2013.01); *A61F 2002/3448* (2013.01); *A61F 2002/3451* (2013.01); *A61F 2002/4623* (2013.01); *A61F 2002/4629* (2013.01); *A61F 2002/4631* (2013.01); *A61F 2002/4638* (2013.01); *A61F 2220/0025* (2013.01); *A61F 2220/0041* (2013.01); *A61F 2220/005* (2013.01); *A61F 2230/0017* (2013.01); *A61F 2250/0006* (2013.01); *A61F 2250/0039* (2013.01); *A61F 2310/00023* (2013.01); *A61F 2310/00029* (2013.01); *A61F 2310/00203* (2013.01); *A61F 2310/00239* (2013.01)

(56) References Cited

U.S. PATENT DOCUMENTS

| | | | |
|---|---|---|---|
| 5,425,778 A | | 6/1995 | Zichner et al. |
| 5,443,508 A | * | 8/1995 | Giampapa ............... 623/23.72 |
| 6,475,243 B1 | | 11/2002 | Sheldon et al. |
| 6,488,713 B1 | * | 12/2002 | Hershberger ............. 623/22.11 |
| 6,537,321 B1 | * | 3/2003 | Horber ..................... 623/22.22 |
| 2002/0068980 A1 | | 6/2002 | Serbousek et al. |
| 2003/0212459 A1 | * | 11/2003 | Gibbs ........................ 623/22.32 |
| 2004/0199258 A1 | | 10/2004 | Marcara |
| 2005/0288793 A1 | | 12/2005 | Dong et al. |
| 2006/0190089 A1 | * | 8/2006 | Montoya et al. .......... 623/22.28 |
| 2007/0142921 A1 | * | 6/2007 | Lewis et al. .............. 623/22.36 |

FOREIGN PATENT DOCUMENTS

| | | |
|---|---|---|
| DE | 42 05 018 | 8/1993 |
| DE | 94 18 963.3 | 1/1995 |
| DE | 195 42 116 A1 | 5/1995 |
| DE | 195 42 116 | 5/1997 |
| DE | 197 46 997 | 4/1999 |
| EP | 0 591 594 | 4/1994 |
| EP | 1 082 949 | 3/2001 |
| EP | 1 082 949 A1 | 3/2001 |
| EP | 1 195 149 | 4/2002 |
| FR | 2 633 823 | 1/1990 |
| FR | 2 827 503 | 1/2003 |
| JP | 02-286159 A | 11/1990 |
| JP | 04-297253 | 10/1992 |
| JP | 07-000434 A | 1/1995 |
| JP | 07-085744 B | 9/1995 |
| JP | 11-347055 A | 12/1999 |
| JP | 2004-537371 T | 12/2004 |
| WO | 03-013397 A2 | 2/2003 |

OTHER PUBLICATIONS

SPH Revision Cups brochure available from http://www.lima.it/en/products.php/34/SPH%20Revision%20Cups; undated; accessed Nov. 10, 2008.

European Search Report of foreign counterpart application DE 20 2006 006 349; dated Nov. 20, 2006; 2 pages.

Office Action of Japanese corresponding counterpart Application No. P2009-505771 dated Oct. 11, 2011.

Examination Report of foreign counterpart Indian Patent Application No. 9001/delnp/2008 dated Nov. 25, 2014, 2 pages.

* cited by examiner

MODULAR HIP IMPLANT

BACKGROUND

The invention generally relates to hip implants, particularly to a modular hip implant comprising a base member in form of an acetabular support shell for being attached to a pelvic bone, and comprising a cup for receiving a hip joint prosthesis, wherein the base member can be attached at the pelvic bone and comprises an accommodation portion for the cup, wherein the cup has an outer shape complementary to the accommodation portion.

Artificial hip joints comprise a hip joint prosthesis insertable into the femur and an acetabular cup to be attached to the pelvic bone. The end of the hip joint prosthesis pointing away from the knee has a spherical shape to engage into the acetabular cup of a hip implant and to form a ball joint together with this cup.

If the pelvis does not offer sufficient osseous substance for safely fastening a simple acetabular cup, an additional support by ring or shell structures is required. These structures can particularly be used in hip joint exchange operations, in which the actual bone loss can only be determined during an operation and after the primary implants have been disassembled. The bone cement used to fix the cup in place also represents one reason for exchanging a cup. Also in the case of a successful cup revision, a later second revision should be expected. Other than the reconstruction of osseous defects by using transplants, an easily-handled, purely cement-free fastening therefore offers significant advantages.

Important aims in the placement of an artificial acetabular cup or revision cup are:

1. primary stable fastening of bone transplants,
2. primary stable fastening of the acetabular cup or support cup,
3. reconstruction of the anatomic hip rotation center, and
4. correct tilting of the cup in the so-called angles inclination and anteversion.

If the two centers of rotation of the two hip joints are connected by a first (horizontal) axis, the anteversion represents the angle of the cup axis with respect to the first (horizontal) axis in a (horizontal) plane through the first (horizontal) axis and a second anterioposterior (horizontal) axis. The inclination represents the angle of the cup axis with respect to the first (horizontal) axis in a (vertical) plane through the first (horizontal) axis and a craniocaudal (vertical) axis. In the human body, the inclination has values in the range between 30° and 50°, whereas values in the range of 5 to 25° are measured in anteversion.

The position of the hip rotation center determines the biomechanics of the hip joint and thus also the life of the implanted endoprosthesis. Additionally, the scope of movement and the transmission of power are defined by the anteversion and by the inclination. If the anteversion is incorrectly chosen, the neck of the femoral shaft prosthesis can abut at the cup edge or the support shell and lever the joint ball out of the cup/shell structure. In the case of an incorrect inclination with a lack of roofing of the joint ball by the acetabular cup, the risk of dislocating the hip joint exists.

When implanting an artificial hip joint, the surgeon should be prepared to take the individual anatomic conditions of the body to be treated into consideration, including the skeletal structure with osseous defects and the muscle/ligament situation of the supporting ligaments. The above-mentioned interrelationships, however, frequently force a compromise between primary stable fastening of support shells at the bone, optimum position of the hip rotation center and correct inclination and anteversion angles. Such difficult implant exchange situations make simple handling with a fully cement-free supply along with an extended adjustment possibility of the anteversion and inclination especially desirable.

Conventional hip implants for revisions are composed of a shell-shaped base member, which predominantly takes over a support function. These implants are usually fastened without cement in a primary stable manner on the pelvic bone. A cup-shaped insert can be inserted in cement-free or cemented manner into this cup by taking the correct inclination and anteversion angle into consideration. This insert accommodates the ball of the hip joint prosthesis.

The cemented fastening of the cup has the advantage that this cup can be adjusted autonomously within certain limits in the shell. The additional introduction of bone cement is, however, undesirable in many cases because of the known disadvantages, and it does not offer a durable support in the shell structure against oscillations occurring between the shell and the cup.

Figure 2:
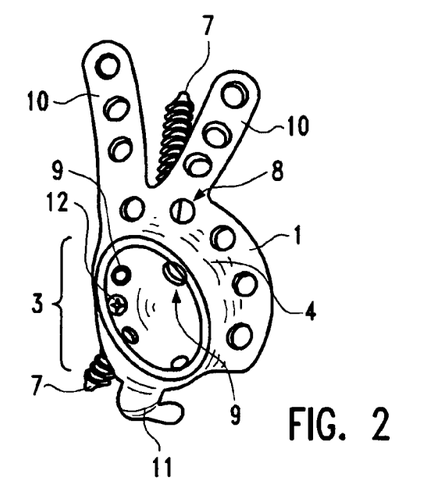
FIG. 2 shows a perspective schematic isolated view of the modular hip implant according to the invention with a cup screwed into the base member.

An acetabular socket support ring is known from U.S. Pat. No. 5,425,778, which permits adjusting the anteversion and inclination of a cement-free cup. Therein, the joint ball is retained and held in position between an inner concavely shaped supporting ring and a second ring that can be screwed into the supporting ring, the ring also being shaped concavely on the section facing the joint ball. A disadvantage of this solution is that when the cup is tilted, it is submersed under the edge level of the supporting ring (U.S. Pat. No. 5,425,778: FIG. 2) and thus the neck of the shaft of the femur can abut against the edge of the supporting shell. This creates the risk that the joint ball can be levered out of the cup. Additionally, this risk cannot be avoided by providing recesses in the supporting ring, because they are connected with a loss of the internal thread in the same. Furthermore, it may occur that individual parts of the supporting ring after operation are twisted relative to each other as a result of heavy mechanic load so that an unfavorable anteversion and/or inclination results. Furthermore, it may be difficult to correctly adjust anteversion and inclination during an operation.

It is an object of the present invention to provide a modular hip implant, which simplifies operation technique when inserting a hip implant into the body to be treated and which can better be adapted to the anatomic requirements of a patient.

A further object of the invention is to provide a shell structure that can be attached at the bone without using cement, in which the bearing insert of a hip joint prosthesis can be introduced (either cemented or cement-free), and which allows the safe adjustment of inclination and anteversion angles also when being attached without cement with a simplified operation technique.

Yet another object of the invention is to provide a modular hip implant with an improved stability.

SUMMARY

According to a first aspect of the invention, a modular hip implant comprises a base member for being attached at a pelvic bone and comprising a cup for receiving a hip joint prosthesis, wherein the base member can be attached to the pelvic bone and comprises an accommodation portion for the cup, wherein the cup has an outer shape complementary to the accommodation portion, and the cup can be attached in the base member, wherein the base member or the cup or both include adjustment means for the variable arrangement of the cup with respect to the base member, and wherein the adjustment means comprise cooperating guides formed in the base member and in the cup.

The solution according to the invention enables a safe adjustment of inclination and/or anteversion of the cup with respect to the base member adapted to the anatomic requirements of the patient during operation or during a revision possibly carried out at a later date. The cooperating guides permit the base member and the cup to be positioned relative to each other to adjust the cup in the base member in a defined manner to achieve a desired inclination and/or anteversion. Furthermore, the guides improve the stability of the hip implant against mechanical stress.

In an advantageous embodiment, the accommodation portion of the base member is formed annularly as a spherical shell open on two sides. Osseous material for a final reconstruction of remaining defects can be introduced through the opening facing the pelvis when the base member is already attached.

In a further advantageous embodiment, the cup is shaped as a spherical shell, particular as a semi-spherical shell. This enables a rotation of the cup relative to the base member and a large contact surface between the cup and the base member.

To provide fastening means for the cup, it is advantageous in a further embodiment to provide a plurality of bores in the accommodation portion and/or the cup.

If at least some of the bores comprise an internal thread, the cup can easily be finally fixed by screwing it into the base member.

If the bores have different diameters, it can easily be determined by the surgeon, which bores of cup and accommodation portion are aligned with one another and match with one another.

For an especially simple insertion of attachment means into the cup and base member, it is particularly advantageous if the corresponding bores in the cup and in the accommodation portion can be aligned with one another by movement of the cup along the guide means.

Optionally, the cup is fixable by a screw connection through the bores in the accommodation portion of the base member. Thereby a stable connection between the cup and the base member can easily be created with low effort.

In other embodiments of the invention, the outer side of the cup is shaped such that the cup can be attached at the base member by means of a cement layer. An attachment of the cup by means of a cement layer is an alternative to the attachment of the cup by means of a screw connection.

According to a further aspect of the invention, a modular hip implant comprises a base member for attachment at a pelvic bone and comprising a cup for accommodating a hip joint prosthesis, wherein the base member can be attached to the pelvic bone and comprises an accommodation portion for the cup, wherein the cup has an outer shape complementary to the accommodation portion, and wherein the cup comprises a first portion with an opening and a second portion, wherein the second portion can be guided through the opening of the first portion and can be attached at the base member, and wherein the second portion is adapted to fix the first part relative to the base member.

Attaching the cup at the base member according to the invention avoids creating a contact between the neck of the shaft of the femur and the mounting of the cup. This reduces the risk of dislocating the artificial hip joint. Furthermore, an improved stability of the attachment of the cup on the base member can be achieved, because the mounting is distant from the exposed upper rim of the cup. Furthermore, the shaping of the upper rim of the cup is no longer restricted by the necessity of attaching a thread.

Optionally, the base member and the second portion of the cup comprise fasteners corresponding to one another to enable a fast and safe connection of these components under surgical conditions.

In particular, the fasteners can comprise an internal thread in the base member and an external thread corresponding thereto on the second part of the cup. As a result, the second part of the cup and the base member can be screwed to one another, thereby providing an especially safe long-term connection between the cup and the base member with respect to micro-movements and oscillations.

The internal thread and the external thread at the second portion of the cup corresponding to the internal thread can be formed as fine threads. This can produce an especially stable connection between the base member and the second portion of the cup.

The base member optionally comprises at least one bore, wherein an axis of the at least one bore is parallel to an axis of the internal thread in the base member. A tool for assembling the hip implant can be inserted into the bore, by the aid of which the second portion of the cup can be screwed to the base member.

In further embodiments of the invention, the second portion of the cup can be attached to the base member by means of a cement layer, which also leads to a very stable connection between the base member and the cup.

The second portion of the cup optionally comprises one or more bores, which are formed to accommodate screws that can be connected to the pelvic bone. If the second portion of the cup is fixedly screwed onto the pelvic bone, the two cup members and the base member are fixed in their relative position to one another and in their position relative to the pelvic bone so that a dislocation of the artificial hip joint or its individual components caused by mechanical stress can substantially be avoided.

The accommodation portion can be formed as a spherical shell open on two sides so that osseous material for the final reconstruction of defects that remain can be introduced through the opening facing the pelvis when the base member is already attached.

The first portion of the cup is suitably formed as a spherical shell open on two sides. Thus, the first portion of the cup has an opening at a central portion suitable to insert the second portion.

In particular, the first portion of the cup can be fixable in several positions relative to the base member. As a result, the geometry of the hip implant can be adapted to the anatomic conditions of the patient during surgery. Thus, the surgeon does not need to select a matching implant from among an available plurality of different implants.

In some embodiments, the first portion of the cup and the base member can comprise a mechanism for pre-locking the first portion of the cup in several positions relative to the base member. This permits the hip implant to be implanted in an easier manner, because the first portion of the cup does need not to be held by hand when inserting the second portion of the cup.

The mechanism for pre-locking the first portion of the cup can comprise a bayonet lock. Thereby, a connection that is easy to manufacture and easy to release can be established between the base member and the first portion of the cup.

In particular, the first portion of the cup and the base member can comprise cooperating guides. Thus, the base member and the first portion of the cup can be positioned relative to one another to adjust the cup in the base member in an especially simple and defined manner to achieve a desired inclination and/or anteversion.

In some embodiments, the guides comprise a groove and a projection at cooperating surfaces of base member and cup. Different angles of inclination and anteversion can be set by simply rotating the cup or its first portion, respectively, in the base member. Providing parts on the cup and base member, which achieve a positive fit and are arranged such that movement (particularly rotation) of the cup with respect to the base member adjusts the inclination corresponding to the angular details stated below concerning the base member, permits a precise adaptation to each individual case.

To adjust the inclination independent of the anteversion, it is advantageous in this embodiment to provide different cups and/or base members, whose respective cooperating guides enable a variation of the combination of different anteversion and inclination angles.

In a further embodiment of the invention, positive fit-forming parts are provided which include special latch positions so that continuously or stepwise variable inclination and anteversion angles can be adjusted in the cup and in the base member in addition to or as an alternative to the cooperating guide means. By providing different cups and/or base members, the inclination and anteversion in this embodiment can be adjusted independently of one another either in an infinitely variable or in a stepwise variable manner. This increases the variability of the use of the modular hip implant and also provides an especially simple and safe handling to adjust the desired inclination and anteversion.

In a further embodiment, the groove is provided on the inner side of the accommodation portion of the base member and the projection is provided on the outer side of the cup. In this advantageous embodiment, inserting the cup into the base member is especially simply. The engagement of groove and projection at the base member and at the cup produces a power-receiving positive-fit interconnection.

In further embodiments, the projection is formed in an annularly circumferential manner. This permits an infinitely variable adjustment of inclination and anteversion angle. It is also advantageous if the groove is formed in a circumferential manner. In other embodiments the projection and the groove can also be discontinuous. In specific embodiments, the projection and the groove can also be reduced to individual posts or recesses arranged in a defined manner.

It turns out to be useful, particularly from the standpoint of simplicity, reliability and cost-effect manufacture, if the cup has a planar rim, which may, in particular, lie in one plane.

The plane of the planar rim of the cup defines a surface normal. In the same manner, a surface and thus an associated surface normal can be defined by the annular projection of the cup. The normal of the plane through the projection and the normal of the plane of the planar rim can, in particular, include an angle $\alpha$ of between about 5° and 30°, in particular between about 5° and 20°, further particularly between about 15° and 20° and further particularly about 17°. As a result, especially favorable anteversion and inclination values can be achieved.

In a corresponding manner, the groove in the accommodation portion of the base member or, in other embodiments, corresponding parts, determine a plane through which a surface normal is defined. The upper rim of the accommodation portion can also define a plane and a respective surface normal. In an advantageous embodiment, the surface normal of the plane defined by the groove is inclined by an angle $\beta$ with respect to the surface normal of the plane defined by the upper rim of the accommodation portion. This angle of inclination $\beta$ may in particular be between about 0° and 30°, in particular between about 5° and 25°, further particularly between about 10° and 22°, or further particularly about 20°.

In an advantageous combination the angle $\beta$ has a value of between about 0° and 30°, in particular in the range between about 5° and 20°, in particular in the range between about 10° and 20° or in particular about. 17°, in particular in combination with an angle $\alpha$ in the range of between about 0° to 30°, in particular between about 5° and 25°, further particularly between about 10° and 22°, and in particular 20°.

In an alternative embodiment, the base member is designed such that a plane is arranged through the groove in the accommodation portion in parallel to a plane defined through the upper rim of the accommodation portion of the base member.

In order to improve the ingrowth behavior, it has proven to be advantageous in an embodiment if the cup and/or the base member are at least partially, preferably fully, made of titanium, titanium alloys or a titanium compound. As an alternative, stainless steel alloys or cobalt-chromium alloys can be used.

In one embodiment the base member comprises two adjoining radially projecting flaps and a tongue opposing the flaps. This permits the base member to be attached especially safely and simply at the pelvic bone.

In this embodiment the flaps may comprise bores, whereby simple screw fastenings are possible.

Generally, one or a plurality of bores can exist in the hip implant to enable an attachment of the hip implant on the pelvic bone and the individual components of the hip implant to one another.

The bores are optionally suitable for accommodating screw connections, which connect the base member and/or the cup with the pelvic bone.

The bores can be closable to prevent the harmful penetration of abrasive particles into the bone or to prevent contact of bone cement with the bone if one or a plurality of bores are not required for attachment. To close the opening, screws and/or plugs can be used. The plugs can for instance be made of polyethylene or a metallic implant material.

The bores can be provided with an internal thread for using angularly stable screws. The use of established dome screws has turned out to be positive in one embodiment.

According to a further aspect of the invention, a modular hip implant comprises a base member, which can be attached to a pelvic bone and which comprises an accommodation portion having an inner shape complementary to a bearing insert of the hip joint prosthesis. The accommodation portion has an opening that can be closed by a closure element, wherein the closure element can be attached to the base member.

The opening makes access to the pelvic bone possible, even after inserting the hip implant. The closure element provides an inner surface at which the bearing insert of the hip joint prosthesis can be attached; e.g., by means of cement.

The closure element optionally has a shape complementary to the bearing insert on a side facing the accommodation portion. This ensures a proper contact between the bearing insert and the closure element.

It can be advantagous if the base member and the closure element comprise attachment means corresponding to one another, which can for instance comprise an internal thread in the base member and an external thread in the closure element corresponding to the internal thread. This can allow a stable and durable connection between the closure element and the base member.

The closure element is optionally adapted to supplement the accommodation portion to form a recess having an inner shape corresponding to the bearing insert of the hip joint prosthesis. Thus, a large contact surface between the bearing insert and the hip implant can be obtained, which can ensure a proper power transmission between the hip implant and the hip joint prosthesis.

The accommodation portion can be formed as a spherical shell open on two sides, and the closure element can be formed as a spherical shell. This creates a spherical shell-shaped inner surface of the hip implant, which can, in particular, be suitable for attaching a spherical bearing insert.

In a further embodiment, the invention is a tool for assembling a modular hip implant. The tool includes a base member attachable to a pelvic bone, and a component adapted to be screwed to a thread at the base member. The base member includes at least one bore, which defines an axis, which is parallel to an axis of the thread on the base member. The tool also includes a guide rod that is insertable into the bore in the base member, a guide sleeve, which is displaceable along the guide rod, and a screw-in instrument that is connected to the guide sleeve. An axis of the screw-in instrument is arranged in parallel to the guide rod.

By means of this tool, screwing the component into the base member can easily be carried out. The guide rod permits the screw-in tool and thus also the thread on the component to be aligned substantially in parallel to the thread in the base member. Thus, a canting of the component can be prevented. As a result, errors during implantation of the hip implant leading to a reduced stability of the hip implant can also be avoided.

The guide rod can have an external thread on one end, with the thread being adapted to be screwed with an internal thread into the bore of the base member. Thus, the guide rod can firmly be secured on the base member during use of the tool.

The screw-in instrument is suitably pivotable around the guide rod. This permits the screw-in instrument to be brought into a position suitable for screwing in the component after inserting the guide rod, and maintains the parallel alignment of the axis of the screw-in tool to the guide rod.

It can be advantageous if the screw-in instrument comprises a means for the detachable attachment of the component of the hip implant on the screw-in instrument. Thus, the component can be brought close to the base member by the aid of the screw-in instrument in an alignment suitable for being screwed into the thread of the base member.

BRIEF DESCRIPTION OF THE DRAWINGS

The invention will now be described in detail with reference to the drawings:

FIG. 8b shows a schematic sectional view of the embodiment shown in FIG. 8a.

DETAILED DESCRIPTION

Figure 1:
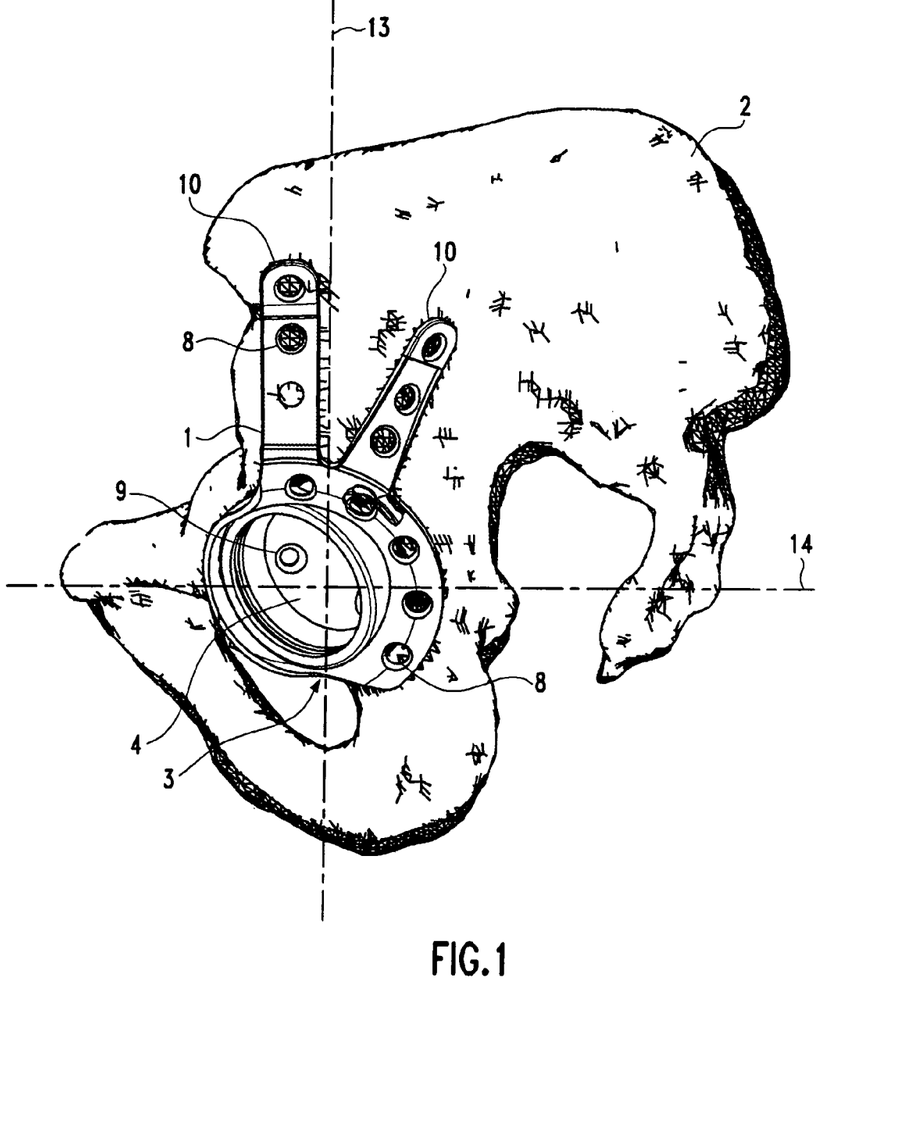
FIG. 1 shows a modular hip implant according to the invention in a state mounted into the pelvic bone in a perspective schematic view.

FIG. 1 shows a modular hip implant according to the invention comprising a base member 1 which is attached to a pelvic bone 2. The base member 1 has a shell-shaped accommodation portion 3. A cup 4 is inserted into the accommodation portion 3.

The base member 1 comprises fasteners for attaching the base member 1 on the pelvic bone. Screws, such as a dome screw 7 (FIG. 2), can be used as fasteners. The fasteners, particularly the dome screws 7, are not shown in FIG. 1. Dome screws 7 are, however, shown in FIGS. 2 and 3. Bores 8 are included into the base member 1. Further bores 9 are also included into the cup 4.

The base member 1 comprises two flaps 10 and a tongue 11. This tongue cannot be seen in FIG. 1, however, it can be seen in FIG. 2 and 3. The flaps 10 are arranged in juxtaposition to one another. They are located on the opposing side of the tongue 11. The flaps 10 are also provided with bores 8, as well as the accommodation portion 3. The tongue 11, which is for instance formed without any bores, is formed in a hook-shaped manner to encompass a part of the pelvic bone 2. To fix the base member 1 on the pelvic bone 2, screws can be screwed into the pelvic bone 2 through the bores 9 in the flaps 10 in addition to the dome screws 7.

The bores 8 and/or 9 can also be formed with an internal thread to enable the introduction of angularly stable screws.

The accommodation portion 3 of the base member 1 is formed concavely and has the shape of an annular shell, which is open towards the bottom, i.e. against the pelvic bone. The cup 4 formed with a corresponding convex outer surface can be inserted into this annular partially shell-shaped concave portion of the accommodation portion of the base member 1, and the cup 4 abuts there. The accommodation portion 3 and the convex outer surface of the cup 4 can each comprise a substantially spherical surface portion, whose radii are designed such that the surface portions of the accommodation portion and the cup rest planarly.

To attach the cup 4 in the base member 1, screws 12 are guided through the bores 8 in the base member 1 and in the cup 4. The bores 8 in the base member 1 can, in particular, have an internal thread into which a connection screw 12, as shown in FIG. 2, engages. By selectively bringing the bores 8 and 9 into alignment, various angular positions of the cup 4 with respect to the base member 1 can be realized. The screw connection gripping through the bores 8 and 9 permanently fixes the cup 4 in the base member 1.

A hip joint prosthesis (not shown) engages into the semispherically formed cup 4, namely a substantially spherical end of an artificial hip joint, particularly an artificial socket that is formed by a bearing insert. The bearing insert can comprise a plastic material, e.g. polyethylene (PE). In special embodiments of the invention, UHMW (Ultra High Molecular Weight) PE or crosslinked PE can be used. As an alternative, the bearing insert can comprise a ceramic material; e.g., aluminum oxide or zirconium oxide ceramics or a metal alloy, e.g. $CoCr_{28}Mo_6$.

In some embodiments the cup 4 can be moved in the accommodation portion of the base member around three axes that are orthogonal with respect to one another. These axes are defined as follows: A first horizontal axis (not shown) extends through the two points of rotation of the two hip joints of the pelvic bone 2. A second horizontal axis 14 is perpendicular to the first horizontal axis and to a vertical axis 13. By rotating the cup around the vertical axis 13, the anteversion can be adjusted. By rotating around the horizontal axis 14, the inclination can be adjusted.

FIG. 2 shows the cup 4 secured by means of the connection screw 12 in the base member 1; i.e., in the accommodation portion 3. Two dome screws 7, or other suitable screws, enable the base member 1 to be fixed to the pelvic bone 2 (not shown). The arrangement of bores 8 and 9 in the base member 1 and in the cup 4 can be varied. Depending on the arrangement of the bores 8 and 9, particularly relative to one another, different angular positions to achieve various adjustments of the inclination and anteversion can be achieved.

The screw 7 that is located closer to the caudal hook can also be formed as a smooth pin in the portion which is in bone contact.

Figure 3:
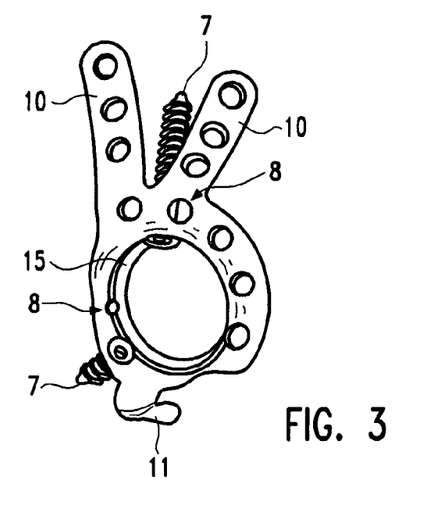
FIG. 3 shows a perspective isolated view of the base member of FIGS. 1 and 2 with a cranial dome screw and a caudally introduced screw.

FIG. 3 shows a singular base member 1 with two dome screws 7. A groove 15 is worked into the annular accommodation portion 3, which is bulged concavely. This groove forms on the base member side a means for guiding and setting the position of the cup inserted. The groove 15 extends annularly through the entire accommodation portion 3. It is also possible to design the groove 15 in an interrupted manner.

Figure 4:
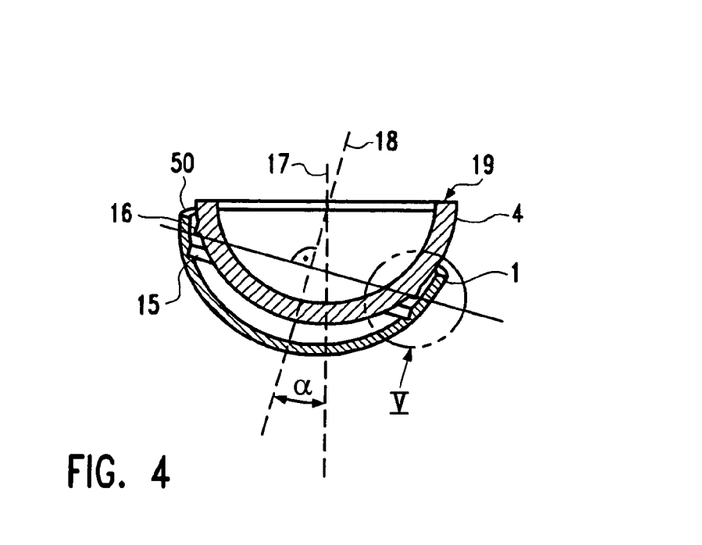
FIG. 4 shows a schematic sectional view through the cup and the base member of FIGS. 1 to 3, wherein the cup includes a projection and the accommodation portion of the base member includes a groove.

FIG. 4 shows the engagement of a means in the form of the projection 16 formed on the outer side of the cup 4 to guide and adjust the position of the inserted cup into the groove 15 of the base member 1. The consequence is a positive fit between the groove 15 and the projection 16 in the state of the cup 4 when it is inserted into the base member 1. The forces acting are forwarded via the groove 15 to the projection 16. The projection 16 extends (e.g., annularly) around the entire outer surface of the cup 4. One or a plurality of interruptions of the projection are possible as an alternative. The projection 16 and the groove 15 form cooperating guides.

In the embodiment shown in FIG. 4 a normal 18 through a plane in which the projection 16 is located is not parallel to a normal 17 of the plane in which an upper rim 19 of the cup is located. The normals 17 and 18 for instance have an angle of approx. 17° between one another. A plane is also defined with respect to an upper rim 50 of the base member. Concerning this plane of the rim 50 of the base member, the plane of the groove in the base member has an angle of approx. 20°. By rotating the cup 4 in the accommodation portion of the base member, an angle between the plane of the rim of the cup and the base member can continuously be set between 3° and 37°.

Figure 5:
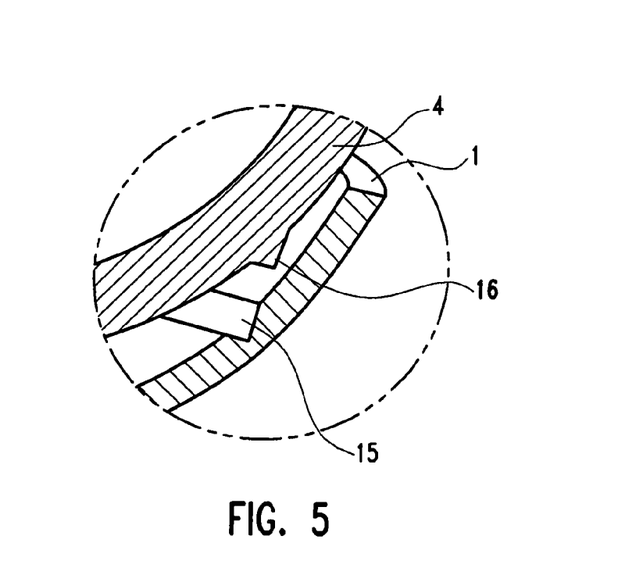
FIG. 5 shows an enlarged detailed view of the portion V of FIG. 4.

FIG. 5 shows the projection 16 and the groove 15 in larger detail. In FIGS. 4 and 5 the fixing means are not yet in engagement with one another, because the cup 4 is not yet completely inserted into the base member 1. In the completely inserted state the projection 16 is arranged in the groove 15.

The angle of the normal through the plane of the guide situated on the cup is characterized as angle $\alpha$ and is measured between the normal 17 through the rim of the cup and the normal 18 through the plane of the guide of the cup 4.

Figure 6:
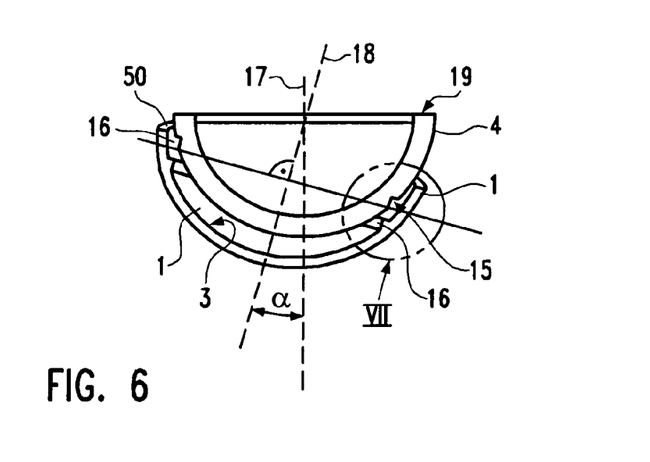
FIG. 6 shows an alternative embodiment of the invention in schematic sectional view through the cup and the base member, in which the cup includes a groove and the base member includes a projection.
Figure 7:
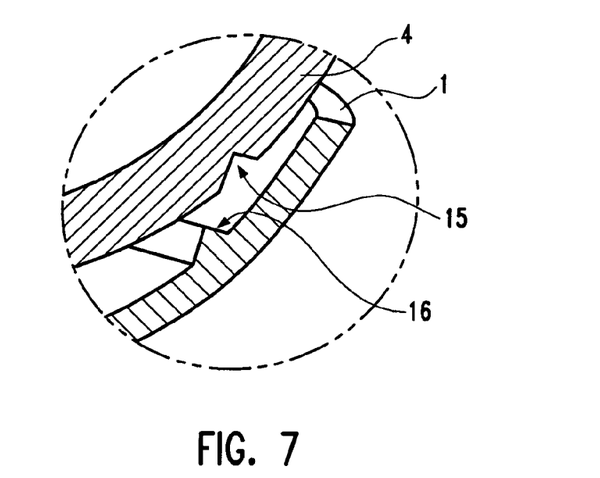
FIG. 7 shows an enlarged detailed view of the portion VII of FIG. 6.

FIGS. 6 and 7 show an alternative embodiment of the modular hip implant. The projection 16 is formed in the base member 1 and the groove 15 is formed on the outer side of the cup 4.

The rim 19 can also have an elevation, e.g. of approx. 10°, which then does not lie on the same level as the rest of the rim 19.

Compared to a rotationally symmetrically formed bearing insert, the rim of the bearing insert 30 (FIG. 10) can also have an elevation in the range of about 10° to 20°.

By rotating the cup in the base member, the values of an angle $\delta$ of the surface normals through the cup rim 19 and through the rim 50 of the accommodation portion can be set in a range from 0° to 34°, if e.g. the annular groove provided in the accommodation portion of the base member is also arranged at an angle of 17° against the surface formed by the upper rim of the accommodation portion. Other adjustment ranges for the angle $\delta$ are possible, depending on the respective angles $\alpha$ and $\beta$, and on the planes determined by the groove and the projection.

Instead of means in which the $\delta$-value and thus the inclination and anteversion angle can be adjusted by rotating the cup, special latch positions can also be provided in the cup 4 and in the base member 1, wherein means for causing a positive fit, i.e. corresponding to the groove 15 and of the projection 16, are arranged such that the individually required values can be set stepwise.

By providing different cups for a base member, anteversion values can also be set independently of the inclination value. It is also possible to provide several grooves or projections in the cup 4 or base member 1. It is also possible to provide both projections as well as grooves on the cup 4 and/or on the base member 1.

The grooves and projections can also be formed sectionwise. In particular embodiments of the present invention, the grooves and projections can also be reduced to posts and recesses arranged in an individually defined manner.

In particular embodiments the cup 4 and the base member 1 are at least partially, and in some embodiments fully, made of titanium or a titanium alloy or compound. TiAl6V4 is especially suitable as a titanium alloy. A base member made of pure titanium enables an especially simple adaptation of the hook and/or flaps to the individual anatomy of the pelvic bone of the patient, since this material is also well deformable at room temperature due to its ductility.

Further embodiments of the present invention are described with reference to FIGS. 8a to 10.

Figure 8A:
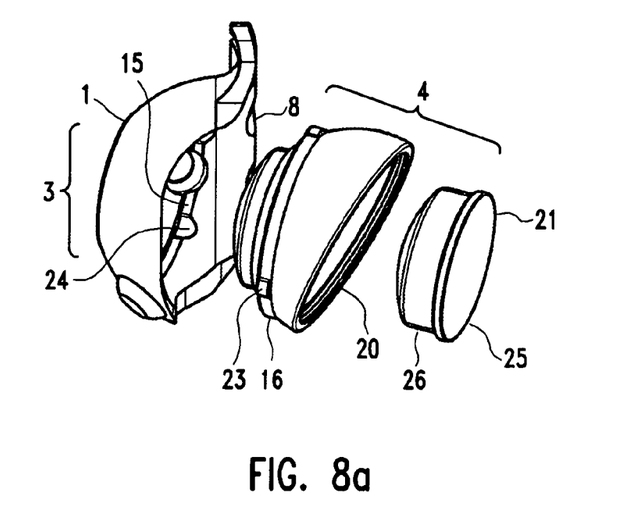
FIG. 8a shows a schematic perspective view of a hip implant according to a further embodiment of the present invention.
Figure 8B:
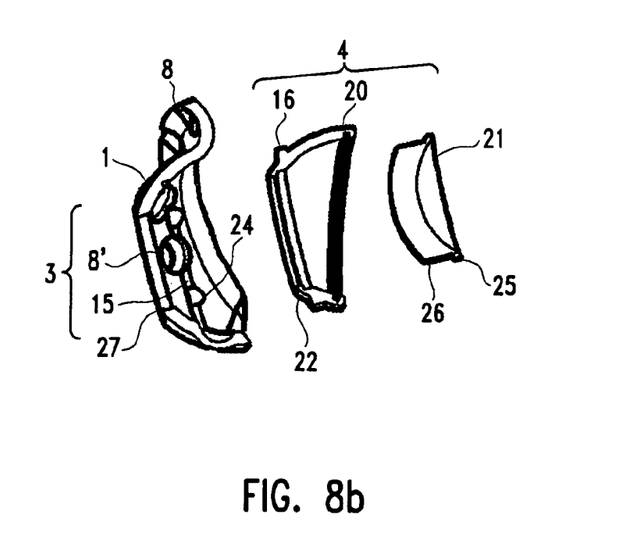

FIG. 8a shows a schematic perspective view of a modular hip implant. FIG. 8b shows a schematic sectional cross-sectional view of the hip implant shown in FIG. 8a. This hip implant comprises a base member 1 and a cup 4, which comprises a first portion 20 and a second portion 21. Contrary to the embodiments described with reference to FIGS. 1 to 7, tongues 11 and flaps 10 are not provided. However, in other embodiments the base member 1 can comprise flaps and a tongue.

The base member 1 is attachable to a pelvic bone. For this purpose, screws can be guided through bores 8 in the base member and can be screwed to the pelvic bone. The bores 8 can be arranged on the circumference of the accommodation portion 3 or in the interior of the accommodation portion 3. In embodiments in which the base member 1 comprises flaps, the bores can also be provided in the flaps. At least one bore 8' (FIG. 8b) is in the interior of the accommodation portion 3. In the illustration of FIG. 8a the bore 8' is covered by the cup 4.

As in the embodiments described above with respect to FIGS. 1 to 7, the bores can comprise an internal thread so that the screws can be attached in an angularly stable manner. To connect the base member 1 with the pelvic bone, dome screws can particularly be used.

In other embodiments, the base member can also be connected by a cement layer to the pelvic bone, wherein a bone cement known to the person skilled in the art can be used. In such embodiments, the bores 8, 8' of the base member can be left out or closed. As an alternative, an attachment by means of cement or an attachment by means of screws can simultaneously be used, whereby a particularly stable attachment can be achieved.

The base member 1 comprises an accommodation portion 3, into which the cup 4 can be inserted. The cup 4 has an outer shape complementary to the accommodation portion 3. In the embodiment shown in FIGS. 9 and 10, the accommodation portion 3 is formed as a spherical shell open on two sides. An opening 27 is provided in the interior of the accommodation portion 3. When the hip implant is assembled, the side of the first portion 20 of the cup 4 facing the base member in FIGS. 8a and 8b rests on the accommodation portion 3 (cf. FIG. 9c). The first portion 20 of the cup 4 is formed as a spherical shell open on two sides, wherein the radii of the accommodation portion 3 and of the second portion 21 of the cup 4 are adapted to one another in such a manner that a planar contact between the accommodation portion 3 and the cup 4 is obtained. As a result, mechanical forces are transmitted in a regular manner from the cup 4 to the base member 1.

The first portion 20 of the cup 4 comprises an opening 22. If the first portion 20 of the cup 4 is inserted into the base member 1, the openings 22, 27 of the first portion 20 and of the base member 1 oppose one another to provide access to the opening 27 of the base member. The openings 22, 27 can have a substantially circular shape. The opening 22 can have a diameter 22, which is at least as large as the diameter of the opening 27 so that the entire opening 27 is also exposed when the first portion 20 of the cup 4 is inserted into the base member 4.

The second portion 21 of the cup 4 has a shape that corresponds to the opening 22 in the first portion 20. In the case of an essentially circular opening 22, the second portion 21 of the cup 4 has a round shape. It can for instance be formed as a spherical shell.

The second portion 21 of the cup 4 is attachable to the base member 1. For this purpose, the second portion 21 of the cup 4 and the base member 1 can comprise fasteners corresponding to one another. In the embodiment shown in FIGS. 8a to 10, the base member 1 comprises an internal thread 29 formed on the circumference of the opening 27. The second portion 21 of the cup 4 comprises an external thread 26 on its circumference. This external thread matches with the internal thread of the base member 1 (cf. FIG. 10). The external thread 26 can be formed in a self-securing manner.

On the side pointing towards the right in the perspective of FIGS. 8a and 8b, the second portion 21 of the cup 4 has a projection 25. A diameter of the outer circumference of the projection 21 is larger than the diameter of the opening 22 in the first portion of the cup 4 so that the second portion 21 of the cup cannot fully pass through the opening 22. The rest of the second portion 21, however, has a smaller outer diameter than the opening 22 so that the second portion of the cup 4 can be guided through the opening 22.

Figure 9A:
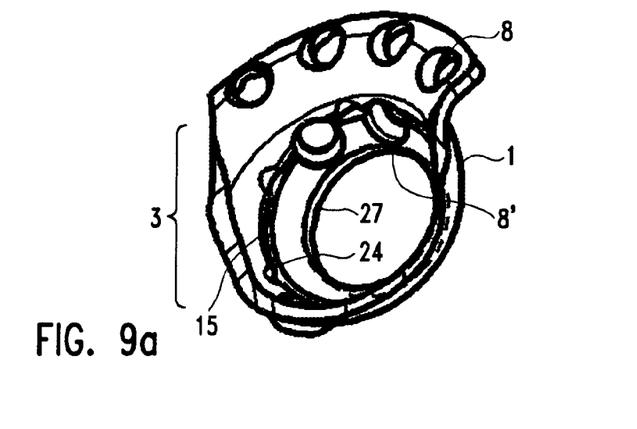
FIGS. 9a to 9d show schematic perspective views of the embodiment shown in FIGS. 8a and 8b in four different stadiums of the assembly.
Figure 9B:
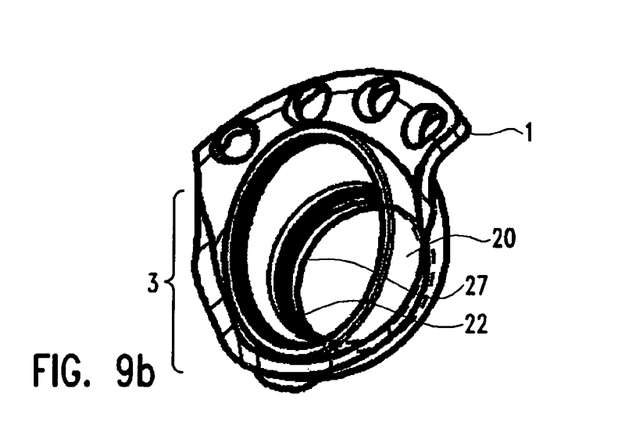

During the implantation of the hip implant, the base member 1 can first of all be fixed to the pelvic bone of the patient by means of screws. The screws and the pelvic bone are not shown in FIG. 9a. Subsequently, the first portion 20 of the cup is inserted into the base member 1, as shown in FIG. 9b, in a manner that the openings 22 and 27 oppose one another. By rotating the first portion 20 relative to the base member 1, inclination and anteversion can be adjusted. For this purpose, a plane in which the upper rim of the first portion 20 of the cup 4 is located can be inclined with respect to an upper rim of the base member, as described above with respect to FIG. 1 to 7. Furthermore, cooperating guides on the first portion 20 of the cup 4 and on the base member similar to those described with respect to the embodiments of FIGS. 1 to 7 can be provided on the cup 4 and on the base member 1. The first portion 20 of the cup 4 for instance comprises a projection 16 and the base member comprises a groove 15 corresponding to the base member. By the bulges 23 of the projection 16 and the recesses 24 of the groove 15, latch positions of the first portion of the shell 20 are defined with a predetermined inclination and anteversion.

In other embodiments of the present invention, the latch positions can be defined by other features of the base member 1 and of the first portion 20 of the cup. In such embodiments, recesses can be provided in the projection 16, and the groove 15 can be interrupted at some positions. In further embodiments, the features of the base member 1 and of the first portion 20 of the cup 4, which define the latch positions, can be provided at positions other than at the groove 15 and the projection 16, e.g. besides the groove 15 or the projection 16.

Figure 9C:
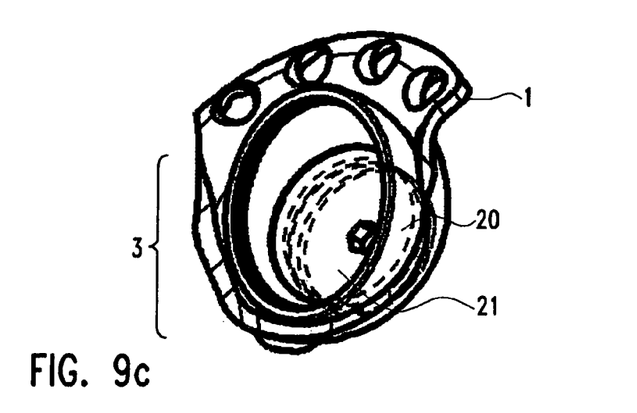

As shown in FIG. 9c, the second portion 21 of the cup 4 is subsequently guided through the openings 27 in the first portion and the external thread 26 of the second portion is screwed to the internal thread 27 of the base member 1. The projection 25 of the second portion then rests on the first portion 20 of the cup, which fixes the first portion 20 relative to the base member 1.

The second portion 21 of the cup 4 can comprise bores 9, which are formed for accommodating screws that can be connected to the pelvic bone. In this manner, the second portion 21 can be attached to the pelvic bone independent of the base member 1, which provides an especially stable support of the second portion 21 of the cup 4.

Figure 9D:
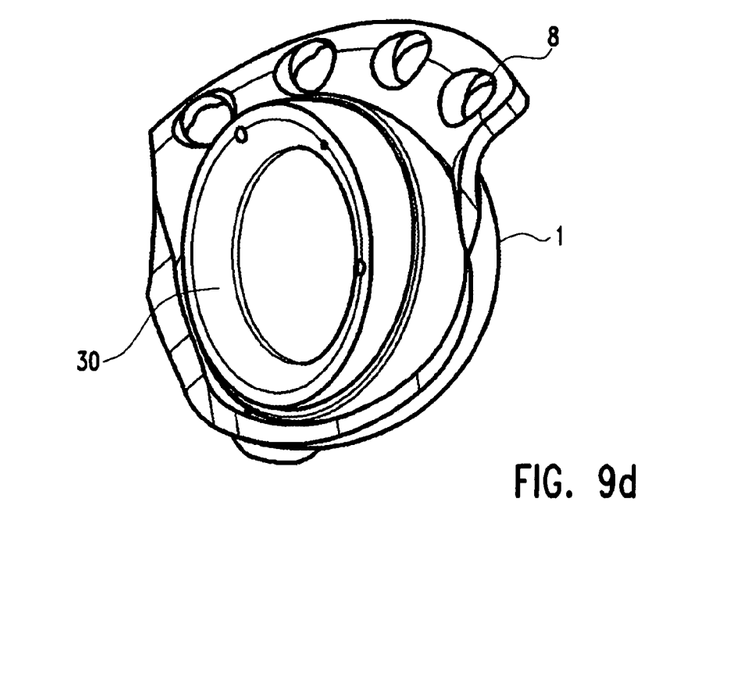
Figure 10:
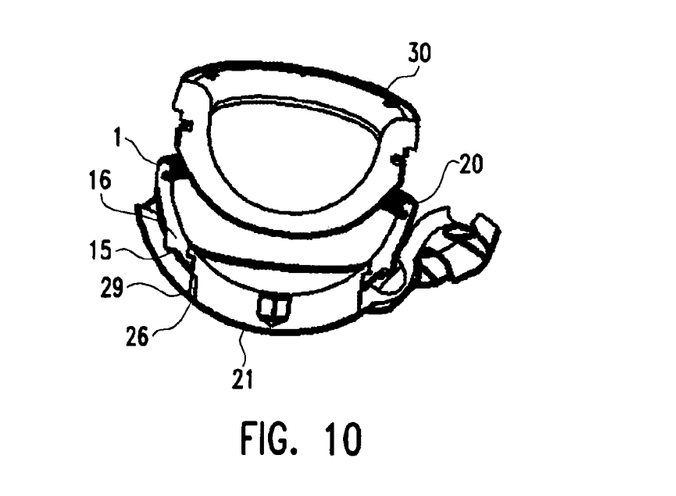
FIG. 10 shows a schematic sectional view through the embodiment shown in FIGS. 8a to 9d in an assembled state.

As shown in FIGS. 9d and 10, a bearing insert 30 can thereupon be attached in the cup 4, which can be done by means known to the person skilled in the art.

In further embodiments, an attachment can also be provided by a cement layer as an alternative or in addition to the attachment of the second portion 21 of the cup by means of the thread 26.

The attachment of the first portion 20 of the cup 4 on the base member need not be implemented by the aid of the projection 25 of the second portion 21 of the cup, as described above with respect to FIG. 8a to 10. In further embodiments, the first portion 20 of the cup 4 can be adapted for being attached by the aid of a cement layer on the base member 1 and the second portion 21 of the cup 4.

A hip implant according to the present invention does not have to comprise a cup 4. In further embodiments of the invention, which will now be described with reference to FIG. 12, the bearing insert 30 of a hip joint prosthesis can be attached in the accommodation portion 3 of the base member 1 by means of a cement layer.

Figure 11A:
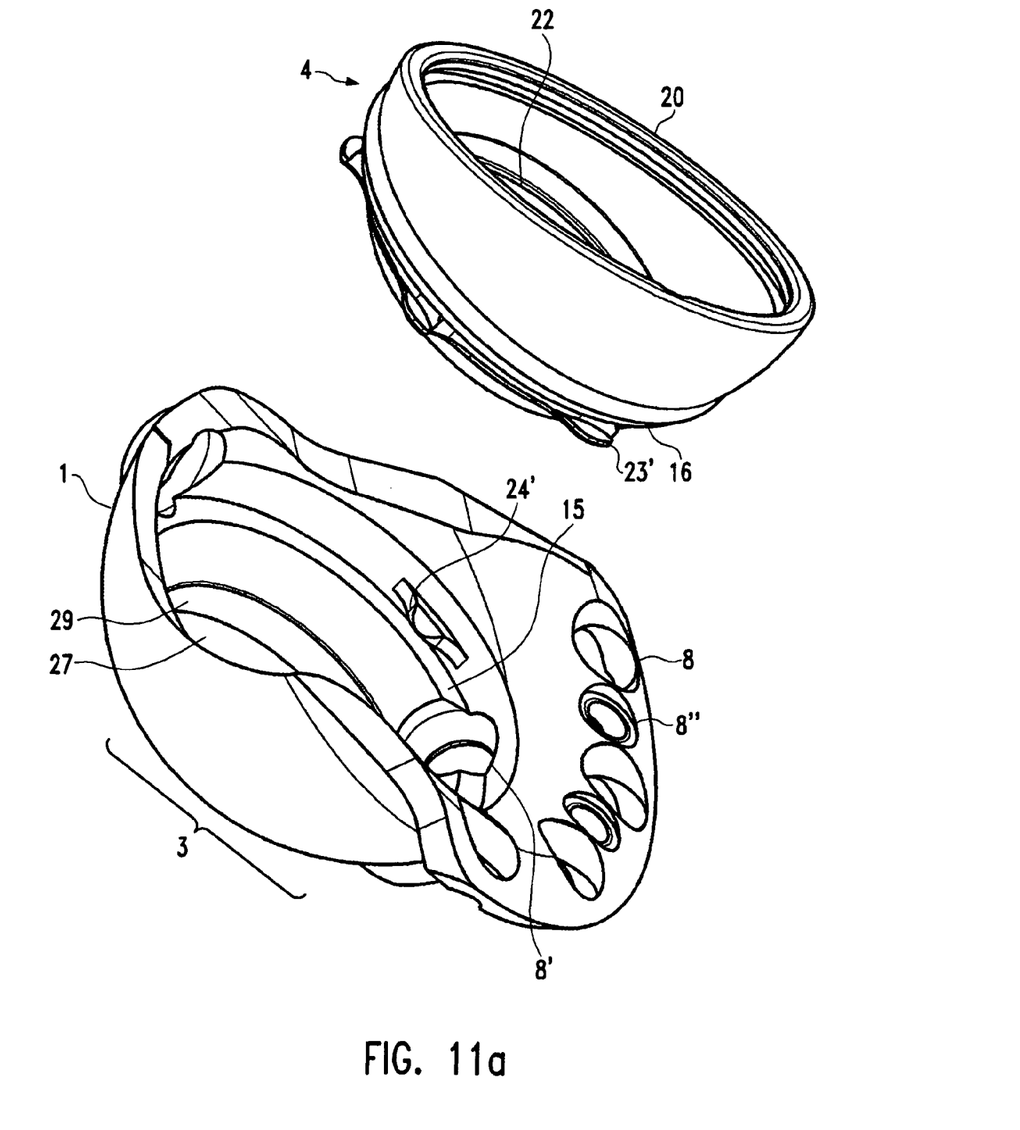
FIG. 11a shows a schematic perspective view of a hip implant according to a further embodiment of the present invention.
Figure 11B:
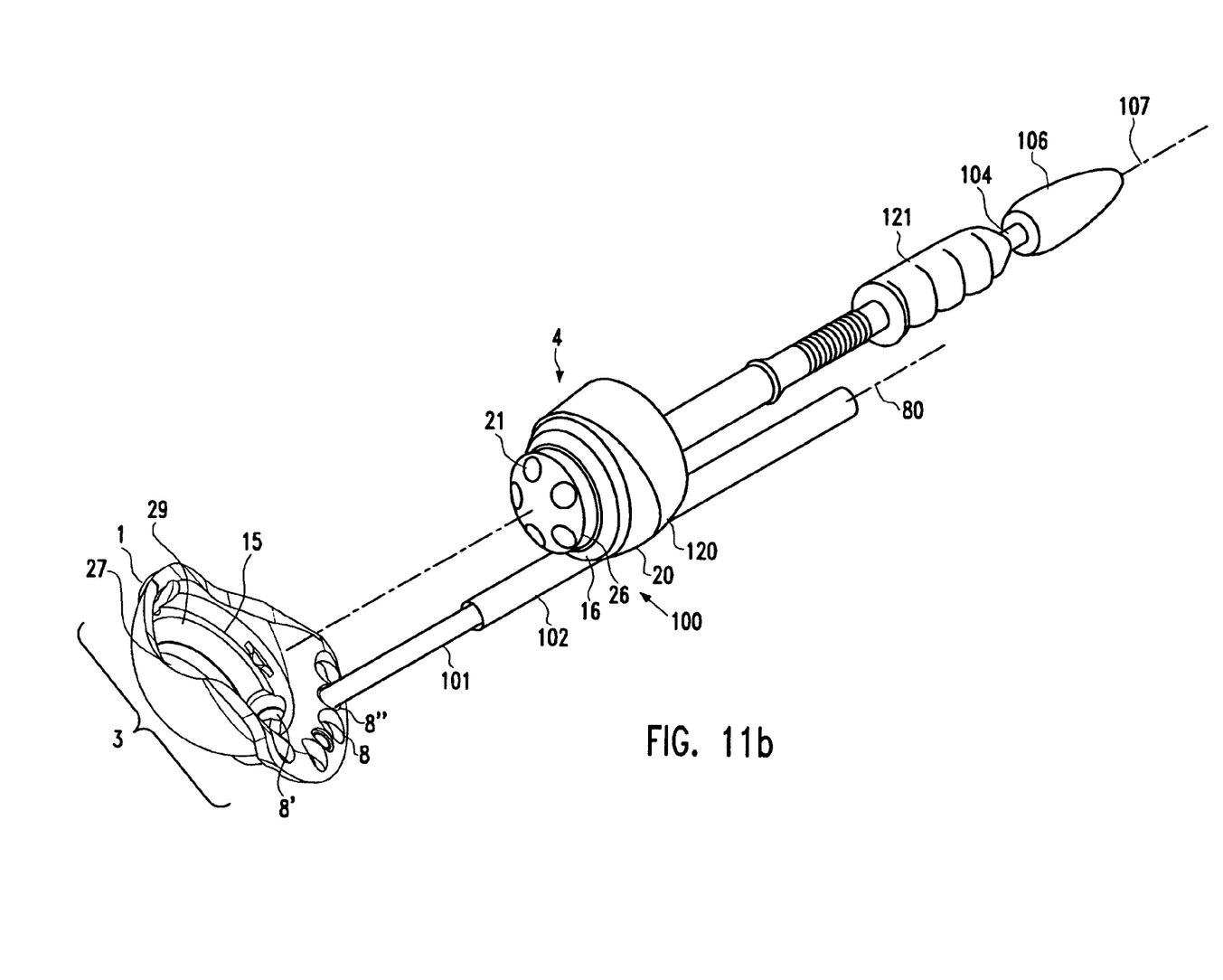
FIG. 11b shows a schematic perspective view of the hip implant shown in FIG. 11a and a tool according to the invention in a stadium of assembly.

FIG. 11a shows a schematic exploded view of a hip implant according to a further embodiment of the present invention. A schematic perspective view of the hip implant in a stadium of assembly is shown in FIG. 11b. The hip implant comprises a base member 1 and cup 4, which comprises a first portion 20 and a second portion 21 (shown in FIG. 11b only). The base member 1 comprises an accommodation portion 3 for the cup and bores 8, 8', which can be provided with an internal thread for accommodating screws. Guides in the form of a groove 15 and of a projection 16 are formed in the base member 1 and in the first portion 20 of the cup 21. A projection is provided at the second portion 21 of the cup 4, with the projection being larger than the diameter of the opening 22 of the first portion 20 of the cup to prevent slipping of the portion 21 through the opening 22. These features can be formed similar to the corresponding features in the embodiments described above with reference to FIGS. 8a to 10, wherein the same reference numerals are used for corresponding features.

An internal thread 29 can be provided in the opening 27 of the base member 1, and an external thread 26 corresponding to the internal thread 29 can be provided on the second portion 21. Thus, the second portion 21 of the cup 4 can be screwed to the base member 1 to fix the first portion 20 and the second portion 21 on the base member 1. The internal thread 29 and the external thread 26 can be formed as fine threads. In a particular embodiment, the internal thread 29 and the external thread 26 can have a pitch in the range of 0.5 to 2. The fine thread improves the stability of the connection between the base member 1 and the cup 4. A sufficiently stable connection which is not released also in the case of changing loads and minimal deformations of the hip implant can particularly be provided by the fine thread with a thickness of the base member in the area of the opening 27 of approx. 3 mm.

The first portion 20 of the cup 4 is fixable in several positions relative to the base member 1. For this purpose, projections 24' are provided on the base member 1. In the perspective of FIG. 11a only one projection 24' can be seen. A plurality of projections 23' are located on the first portion 20 of the cup 4. In order to pre-lock the first portion 20 on the base member 1, one of the projections 23' can be inserted adjacent the projections 24'. Subsequently, the first portion 20 of the cup 4 can be rotated such that a respective one of the projections 23' each rests below each projection 24'.

The projections 23' and 24' form a bayonet lock to prevent the first portion 20 of the cup 4 from falling out of the base member 1. The projections 23' on the first portion 20 of the cup 4 and the projections 24' in the base member 1 are arranged symmetrically so that the first portion 20 can be attached to the base member 1 in several positions to adapt the anteversion and inclination of the hip implant to the anatomy of the patient.

FIG. 11b shows a schematic perspective view of the hip implant in a stadium of assembly.

In order to pre-lock the first portion 20 of the cup 4 and for screwing in the second portion 21 of the cup 4 in the base member 1, a tool 100 can be used. The tool 100 comprises a guide rod 101. The guide rod 101 can comprise an external thread on one end. An internal thread corresponding to this external thread is provided in a bore 8" in the base member 1. An axis 80 of the bore 8" is substantially parallel to an axis 107 of the internal thread 29 in the base member. If the guide rod 101 is screwed into the bore 8", the guide rod 101 is substantially parallel to the axis 107 of the internal thread. 29.

The tool 100 further comprises a guide sleeve 102, which encloses the guide rod 101 and which is displaceable along the guide rod 101. A screw-in instrument 104 is attached on the guide sleeve 102 through a support (which cannot be seen in the perspective of FIG. 11b). The screw-in instrument is rotatable around an axis, which is parallel to the axis of the guide rod 101. The screw-in instrument 104 can for instance be formed as a screw driver and can have a handle 106 as well as a blade, wherein the blade is adapted to engage into a screw head attached at the second portion 21 of the cup 4. The second portion 21 of the cup can for instance have a hexagon socked screw head.

The tool 100 further comprises an adapter 120, which is releasably connected to the first portion 20 of the cup 4, e.g. by a click mechanism. The adapter 120 can be connected to a handle 121 which can have a longitudinal bore, through which the screw-in instrument 104 is guided, wherein the screw-in instrument 104 and the second portion 21 of the cup 4 are rotatable relative to the adapter 120 and to the first portion 20.

The distance between the screw-in tool 104 and the guide rod 101 is substantially equal to a distance between the axis 80 of the bore 8" and the axis 107 of the internal thread 29. If the guide rod 101 is inserted into the bore 8", the screw-in tool 104 can be aligned by pivoting the guide sleeve 102 around the guide rod 101 in a manner that its longitudinal axis coincides with the axis 107 of the internal thread 29.

To insert the cup 4 into the base member 1, first the guide rod 101 is screwed into the bore 8" and the guide sleeve 102 is plugged over the guide rod 101 to align the axis of the screw-in instrument 104 substantially parallel to the axis 107 of the internal thread 29. Subsequently, the tool 101 is turned around the guide rod 101 until the axis of the screw-in instrument 104 substantially coincides with the axis of the internal thread 29. Thereupon, the first portion 20 of the cup 4 can be inserted into the base member 1 and can be pre-fixed by rotation of the handle 121 by the aid of the bayonet lock formed by the projections 23', 24'. Subsequently, the second portion 21 of the cup 4 of the screw-in tool 104 can be screwed to the base member 1. Subsequently, the screw-in tool 104 can be retracted and the adapter 102 can be released from the first portion 20 of the cup 4, and the guide rod 101 can be screwed out of the bore 8".

Figure 12:
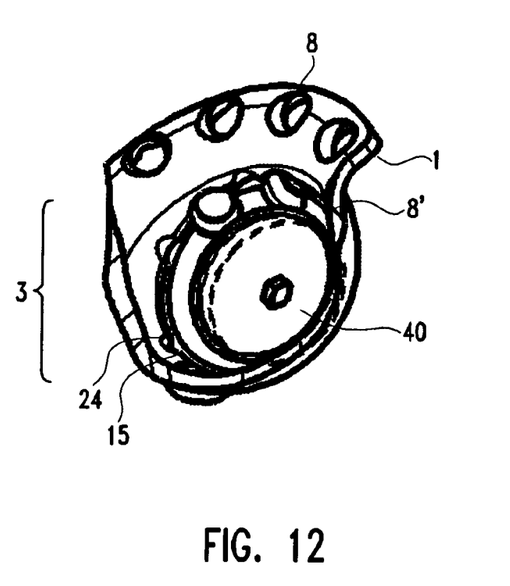
FIG. 12 shows a schematic perspective view of a hip implant according to a still further embodiment of the present invention.

Because the tool 100 enables an alignment of the first portion 20 and the second portion 21 of the cup 4 relative to the base member 1, the second portion 21 can be precisely screwed to the base member 1. As a result, canting of the external thread 26 and of the internal thread 19 can be avoided. Such canting may particularly occur when screwing-in the second portion 21 of the cup 4 freehand, particularly in embodiments of the present invention in which the external thread 26 and the internal thread 29 are formed as fine threads, FIG. 12 shows a schematic perspective view of the base member 1 after attachment by means of screws (not shown) similar to the screws 7 shown in FIG. 2 and 3 in the pelvic bone of the patient (not shown). The base member 1 corresponds to the base member of the embodiment described above with respect to FIGS. 8a to 10.

A closure element 40 is attached in the opening 27 of the base member, which replaces the second portion 21 of the cup 4 that is used in the embodiment described above with respect to FIGS. 8a to 10. The closure element 40 can be attached to the base member 1. For this purpose, the closure element 40 can have an external thread that can be screwed to the internal thread 29 in the opening 27 of the base member 1.

The side of the closure element 40 facing the accommodation portion 3 has a shape which—as well as the inner shape of the accommodation portion—is complementary to the bearing insert of the hip joint prosthesis. In an embodiment of the invention, in which the accommodation portion 3 is formed as a spherical shell open on two sides, the closure element 40 can for instance have the shape of a spherical shell so that the closure element 40 supplements the accommodation portion 3 to form a recess with an inner shape in the design of a spherical shell, if the closure element 40 is aligned with the accommodation portion 3 of the base member 1. The closure element 40 can generally be adapted to supplement the accommodation portion 3 to form a recess with an inner shape complementary to the bearing insert of the hip joint prosthesis. This allows the bearing insert to be attached without problem.

In some embodiments of the present invention, the closure element 40 can comprise openings that can be closed with screws and/or plugs. In other embodiments, the closure element 40 can be formed without any openings. Advantageously, a contact between the cement and the bone can substantially be prevented that way, so that disadvantageous influences of the cement on the bone substance can substantially be avoided.

The invention claimed is:

1. A modular hip implant comprising a base member for attachment to a pelvic bone, and comprising a cup for accommodating a hip joint prosthesis, wherein the base member comprises an accommodation portion for the cup, the accommodation portion having an opening for receiving osseous material through the opening, an internal thread being formed on a circumference of the opening, wherein the cup has an outer shape complementary to the accommodation portion, wherein the cup comprises a first portion with an opening and a second portion, the second portion comprising an external thread that matches with said internal thread wherein the second portion is guidable through the opening of the first portion and attachable to the base member, by screwing said external thread to said internal thread, wherein the second portion is adapted to fix the first portion relative to the base member wherein the first portion of the cup is fixable in a plurality of positions relative to the base member, and wherein the first portion of the cup and the base member comprise a mechanism for pre-locking the first portion of the cup in the plurality of positions relative to the base member, the mechanism for pre-locking the first portion of the cup comprising a bayonet lock.

2. A hip implant as claimed in claim 1, wherein the internal thread formed in the opening of the accommodation portion and the corresponding external thread at the second portion of the cup are formed as fine threads.

3. A hip implant as claimed in claim 1, wherein the base member comprises at least one bore, wherein an axis of the at least one bore is arranged substantially parallel to an axis of the internal thread formed in the opening of the accommodation portion.

4. A hip implant as claimed in claim 1, wherein the second portion of the cup is attachable to the base member by means of a cement layer.

5. A hip implant as claimed in claim 1 wherein said second portion of the cup is formed as a substantially spherical shell.

6. A hip implant as claimed in claim 1, wherein the first portion of the cup and the base member comprise cooperating guides.

7. A hip implant as claimed in claim 6, wherein the guides comprise a groove and a projection.

8. A hip implant as claimed in claim 1, wherein the base member comprises at least one bore, said at least one bore being adapted for accommodating an angularly stable screw for connecting the base member with the pelvic bone.

* * * * *